United States Patent [19]

Inoue et al.

[11] Patent Number: 4,615,912
[45] Date of Patent: Oct. 7, 1986

[54] PROVIDING HYDROPHOBIC SURFACES ON HYDROPHILIC INORGANIC MATERIALS WITH METAL GLYCOLATES

[75] Inventors: Tetsuyu Inoue, Warabi; Kouji Tsuruga, Omiya; Masashi Harada, Yokohama, all of Japan

[73] Assignee: Adeka Argus Chemical Co., Ltd.,, Saitama, Japan

[21] Appl. No.: 636,526

[22] Filed: Aug. 1, 1984

[30] Foreign Application Priority Data

Aug. 10, 1983 [JP] Japan .................. 58-146029

[51] Int. Cl.$^4$ ............ B05D 7/00; C04B 14/00
[52] U.S. Cl. .................. 427/212; 106/288 B; 106/288 Q; 427/215; 427/216; 427/217
[58] Field of Search ............ 106/288 Q, 288 B, 299, 106/286.4, 286.5; 427/215, 216, 217, 212

[56] References Cited

U.S. PATENT DOCUMENTS 3,905,936 9/1975 Hawthorne ................ 427/216 X

Primary Examiner—Thurman K. Page

[57] ABSTRACT

Hydrophilic inorganic materials are provided with a hydrophobic surface by treatment with a metal glycolate compound having the formula:

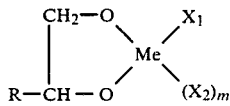

wherein:

Me is Sn, Ti, Zr or Al;
when Me is Sn, Ti or Zr, m is 1, and when Me is Al, m is 0;
R is alkyl having from about eight to about fifty carbon atoms;
$X_1$ and $X_2$ are independently selected from the group consisting of $-R_1$, $-OR_1$, $-OCOR_1$, $-SR_1$, $-S(CH_2)_nCOOR_1$, $-OSO_2-R_1$, $-SR_2OCOR_1$,

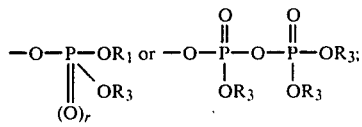

$X_1$ and $X_2$ can be combined to form

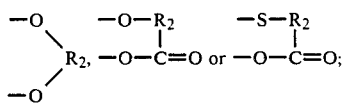

$R_1$ is selected from the group consisting of alkyl having from one to about eighteen carbon atoms; alkenyl having from three to about eighteen carbon atoms; cycloalkyl having from five to about eight carbon atoms; and aryl and alkaryl having from six to about eighteen carbon atoms;
$R_2$ is alkylene having from one to about fifty carbon atoms;
$R_3$ is selected from the group consisting of hydrogen, alkyl having from one to about eighteen carbon atoms; alkenyl having from three to about eighteen carbon atoms; cycloalkyl having from five to about eight carbon atoms; and aryl and alkaryl having from six to about eighteen carbon atoms;
r is 0 or 1.

21 Claims, No Drawings

PROVIDING HYDROPHOBIC SURFACES ON HYDROPHILIC INORGANIC MATERIALS WITH METAL GLYCOLATES

Inorganic materials have been widely used as fillers, pigments, and reinforcing agents for organic polymers. While the surfaces of such inorganic materials are hydrophilic the polymers are hydrophobic. The result is a loss in mechanical strength such as impact strength of the polymer and processability may be more difficult.

To overcome this difficulty, it has been proposed that inorganic materials be surface-treated with organo-titanates or organo-zirconates. Various organo-titanates for this purpose are described in U.S. Pat. Nos. 3,697,475, 3,804,937, 4,080,353, 4,087,402, 4,094,853, 4,096,110, 4,098,758, 4,122,062, 4,152,311, 4,192,792, 4,261,913 and 4,277,415. However, these do not sufficiently alleviate the problems in loss of mechanical strength and processability. In addition, the organo-titanates are unstable to moisture.

In accordance with this invention, it has been determined that polymers filled with hydrophilic inorganic materials surface-treated with metal glycolates as defined below to render their surfaces hydrophobic do not display loss in mechanical strength or problems in processability. Moreover, these metal glycolates are resistant to decomposition or hydrolysis in the presence of water.

The hydrophobing surface treatment for hydrophilic inorganic materials of this invention employs metal glycolate compounds having the following formula:

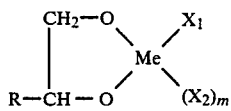

wherein:
Me is Sn, Ti, Zr or Al;
when Me is Sn, Ti or Zr, m is 1, and when Me is Al, m is 0;
R is alkyl having from about eight to about fifty carbon atoms;
$X_1$ and $X_2$ are independently selected from the group consisting of $-R_1$, $-OR_1$, $-OCOR_1$, $-SR_1$, $-S(CH_2)_nCOOR_1$, $-OSO_2-R_1$, $-SR_2OCOR_1$,

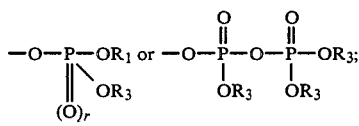

$X_1$ and $X_2$ can be combined to form

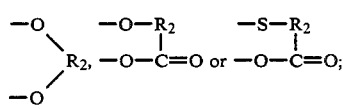

$R_1$ is selected from the group consisting of alkyl having from one to about eighteen carbon atoms; alkenyl having from three to about eighteen carbon atoms; cycloalkyl having from five to about eight carbon atoms; and aryl and alkaryl having from six to about eighteen carbon atoms;

$R_2$ is alkylene having from one to about fifty carbon atoms;

$R_3$ is selected from the group consisting of hydrogen, alkyl having from one to about eighteen carbon atoms; alkenyl having from three to about eighteen carbon atoms; cycloalkyl having from five to about eight carbon atoms; and aryl and alkaryl having from six to about eighteen carbon atoms;

r is 0 or 1.

Exemplary alkyl represented by R include nonyl, octyl, isooctyl, tert-octyl, 2-ethylhexyl, nonyl, isononyl, tert-nonyl, decyl, isodecyl, undecyl, dodecyl, tetradecyl, hexadecyl, heptadecyl, octadecyl, nonadecyl, eicosyl, docosyl, tricosyl, tetracosyl, hexacosyl, octacosyl, triacontyl, dotriacontyl, tetratriacontyl, hexatriacontyl, tetracontyl and dotetracontyl; R is preferably alkyl having more than ten carbon atoms.

Exemplary alkyl represented by $R_1$ and $R_3$ include methyl, ethyl, propyl, isopropyl, butyl, isobutyl, secbutyl, tert-butyl, amyl, iso-amyl, tert-amyl, hexyl, heptyl, octyl, isooctyl, 2-ethylhexyl, nonyl, isononyl, decyl, undecyl, dodecyl, tridecyl, tetradecyl, pentadecyl, hexadecyl, octadecyl; exemplary cycloalkyl include cyclopentyl, cyclohexyl, cycloheptyl, cyclooctyl; methyl cyclohexyl, dimethyl cyclohexyl, methyl cycloheptyl; and Exemplary alkenyl represented by $R_1$ and $R_3$ are vinyl, allyl, hexenyl, dodecenyl, hexadecenyl and octadecenyl; exemplary aryl and alkaryl include phenyl, benzyl, xylyl, mesityl, ethyl phenyl, phenethyl, propyl phenyl, butyl phenyl, octyl phenyl, nonyl phenyl and dodecyl phenyl; naphthyl.

Exemplary alkylene represented by $R_2$ are methylene, ethylene, 1,2-propylene, 1,3-propylene, 1,2-butylene, 1,4-butylene, 1,4-pentylene, 1,6-hexylene, 1,5-heptylene, 1,2-nonylene, 1,6-octylene, 1,8-octylene, 1,2-decylene, and 1,2-octadecylene.

These organic radicals can be substituted by one or more of halogen, amino, nitro, hydroxy, carboxy, epoxy, alkoxy, alkylmercapto, ester or cyano, in the chain or as side chains, and they can include oxygen, sulfur or nitrogen in the chain.

These metal glycolate compounds can be easily prepared by reacting the corresponding metal lower alkoxide with the corresponding 1,2-glycol and $H-X_1$ and/or $H-X_2$. The compounds represented by $H-X_1$ or $H-X_2$ are alcohols or phenols of $R_1OH$; carboxylic acids of

mercaptans of $HSR_1$; mercaptocarboxylic acid esters of $HSR_2COOR_1$; mercaptoalcohol esters of $HSR_2OOCR_1$; sulfonic acids of $HSO_3R_1$; phosphites or phosphates

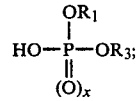

or pyrophosphates of

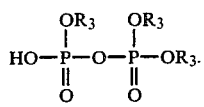

Exemplary alcohols or phenols of $R_1OH$ include methyl alcohol, ethyl alcohol, propyl alcohol, isopropyl alcohol, butyl alcohol, sec-butyl alcohol, isobutyl alcohol, tert-butyl alcohol, amyl alcohol, isoamyl alcohol; hexyl alcohol, isohexyl alcohol, heptyl alcohol, octyl alcohol, isooctyl alcohol, nonyl alcohol, decyl alcohol, dodecyl alcohol, tridecyl alcohol, tetradecyl alcohol, hexadecyl alcohol, octadecyl alcohol, allyl alcohol, oleyl alcohol, cyclohexyl alcohol, benzyl alcohol; phenol butyl phenol, amyl phenol, hexyl phenol, heptyl phenol, octyl phenol, nonyl phenol and dodecyl phenol.

Exemplary carboxylic acids include aliphatic and aromatic carboxylic acids, such as stearic acid, isostearic acid, palmitic acid, ricinoleic acid, linoleic acid, lauric acid, myristic acid, oleic acid, caproic acid, caprylic acid, 2-ethylhexanoic acid, neodecanoic acid; benzoic acid; acrylic acid, methacrylic acid, p-aminobenzoic acid, aminopropionic acid, aminocaprylic acid and epoxystearic acid.

Exemplary mercaptans include octyl-, dodecyl-, stearyl- and benzyl-mercaptan.

Exemplary mercaptocarboxylic acid esters include iso-octyl-, 2-ethylhexyl-, decyl-, dodecyl-, myristyl- and stearyl-thioglycolate and iso-octyl mercaptopropionate.

Exemplary mercapto-alcohol esters include mercaptoethyl oleate, mercaptoethyl laurate and mercaptoethyl stearate.

Exemplary sulfonic acids include benzene-, p-aminobenzene- and octadecane-sulfonic acid.

Exemplary phosphites, phosphates and pyrophosphates include dibutyl-, diamyl-, dihexyl-, dioctyl-, ditetradecyl-, dihexadecyl-, dioctadecyl-, diphenyl-, dixylyl-, bis(dodecylphenyl)- and dibenzyl-phosphite, phosphate and pyrophosphate.

Typical examples of metal glycolates employed in the invention are:

Isopropoxy isostearoyloxy titanium $C_{12-14}$alkylene glycolate
Isopropoxy isostearoyloxy titanium $C_{16-18}$alkylene glycolate
Diisostearoyloxy titanium $C_{16-18}$alkylene glycolate
Diisopropoxy titanium $C_{16-18}$alkylene glycolate
Titanium bis($C_{16-18}$alkylene glycolate)
Isopropoxy oleoyloxy titanium $C_{16-18}$alkylene glycolate
Isopropoxy acryloyloxy titanium $C_{12-14}$alkylene glycolate
Isopropoxy titanium diisooctylphosphate $C_{10-12}$alkylene glycolate
Methoxy isostearoyloxy titanium $C_{12-14}$alkylene glycolate
Isopropoxy titanium dodecylbenzenesulfonate $C_{16-18}$alkylene glycolate
Ethoxy titanium dioctyl pyrophosphate $C_{16-18}$alkylene glycolate
Isopropoxy dodecylmercapto titanium $C_{16}$alkylene glycolate
Methoxy octylmercapto titanium $C_{18}$alkylene glycolate
Ethoxy 2-ethylhexylmercapto titanium $C_{20-30}$alkylene glycolate
Titanium β-oxypropionate $C_{10}$alkylene glycolate
Titanium oxyacetate $C_{30-40}$alkylene glycolate
Isopropoxy oleoyloxyethyl thio titanium $C_{30}$alkylene glycolate
Isopropoxy octadecyloxy titanium $C_{20}$alkylene glycolate
Methoxy octyltin $C_{16-18}$alkylene glycolate
Methoxy isostearoyloxytin $C_{16-18}$alkylene glycolate
Dibutoxytin $C_{18}$alkylene glycolate
Methoxy tin oleate $C_{12-14}$alkylene glycolate
Isopropoxy tin dodecylbenzenesulfonate $C_{12}$alkylene glycolate
Butyl tin dioctyl pyrophosphate $C_{12-14}$alkylene glycolate
Butoxy butoxycarbonylethyl tin $C_{16}$alkylene glycolate
Isopropoxy methyl tin $C_{16-18}$alkylene glycolate
Methyl tin isooctoate $C_{16-20}$alkylene glycolate
Tin β-oxypropionate $C_{18}$alkylene glycolate
Octyl tin 2-ethylhexylthioglycolate $C_{16-18}$alkylene glycolate
Butyl tin dodecyl mercaptide $C_{16-18}$alkylene glycolate
Tin oxyacetate $C_{16-18}$alkylene glycolate
Dioctyl tin $C_{20}$alkylene glycolate
Dibutyl tin $C_{16}$alkylene glycolate
Octadecyloxy zirconium isostearate $C_{18}$alkylene glycolate
2-Ethylhexyloxy zirconium isostearate $C_{10}$alkylene glycolate
Isopropoxy zirconium isostearate $C_{12}$alkylene glycolate
Ethoxyzirconium caprylate $C_{14}$alkylene glycolate
Isopropoxy zirconium isostearate $C_{16}$alkylene glycolate
Dibutoxy zirconium $C_{16-18}$alkylene glycolate
Dibutoxy zirconium oleate $C_{12-16}$alkylene glycolate
Methoxy zirconium isooctoate $C_{16-18}$alkylene glycolate
Methoxy zirconium dioctyl pyrophosphate $C_{16-18}$alkylene glycolate
Zirconium β-oxypropionate $C_{16-18}$alkylene glycolate
Isopropoxy zirconium dodecylmercaptide $C_{12-14}$alkylene glycolate
Ethoxy zirconium dodecylbenzenesulfonate $C_{10}$alkylene glycolate
Isopropoxy aluminum $C_{12-14}$alkylene glycolate
sec-Butoxy aluminum $C_{16-18}$alkylene glycolate
Aluminum isostearate $C_{12-14}$alkylene glycolate
Aluminum isopropylmaleate $C_{16-18}$alkylene glycolate
t-Butoxy aluminum $C_{16-18}$alkylene glycolate
Aluminum aminoacetate $C_{16-18}$alkylene glycolate To obtain the desired hydrophobic surface effect, the amount of metal glycolate compound used is at least 0.01 part, preferably from 0.5 to 10 parts, per 100 parts of hydrophilic inorganic material. An unknown hydrophobing reaction with the metal glycolate takes place on the surface of the hydrophilic inorganic material, forming a hydrophobic surface layer of organic nature involving organic groups derived from the metal glycolate on the inorganic material. While the unmodified inorganic material is difficult to disperse in a hydrophobic organic medium, because it is hydrophilic, the treated surface is hydrophobic, and the modified inorganic material is readily dispersed in such organic media.

Accordingly, the hydrophobing surface treatment can be carried out by dispersing the metal glycolate compound in a hydrophobic organic medium, such as a low molecular weight liquid or inert solvent, or a higher molecular weight polymeric solid, and then adding the inorganic material. Alternatively, the metal glycolate may be first reacted with the inorganic material in the absence of a hydrophobic organic medium, and thereafter admixed with the organic medium.

The hydrophilic inorganic material can be particulate or fibrous, and of any shape or size, but the surface must be reactive with the hydrolyzable group of the metal glycolate.

A most important class of hydrophilic inorganic materials is fillers for polymeric materials, and another important class is pigments for polymeric materials.

Examples of inorganic materials including fillers and pigments are metals, such as iron, aluminum, steel, copper, brass, bronze, titanium alloys, magnesium, monel, nickel alloys, stainless steel; inorganic compounds such as clay, such as bentonite, montmorillonite, attapulgus, Fullers earth, carbon black, calcium carbonate, barium sulfate, silica, mica, aluminum trihydrate, α-alumina, β-alumina, magnesium hydroxide, calcium silicate, aluminum silicate, talc, glass, quartz, vermiculite, asbestos, metal oxides of zinc, magnesium, lead, calcium, aluminum and iron, titanium dioxide, ferrite, zinc chromate and ultramarine blue.

The particle size of the particulate material is in no way critical, but generally the particles will not be greater than 1 mm, preferably from 0.1 micron to 500 microns, in size.

The following Examples illustrate preparation of these metal glycolates:

EXAMPLE A

Preparation of isopropoxy isostearoyloxy titanium C$_{16-18}$alkylene glycolate

Tetraisopropyl titanate 284 g, toluene 300 g and C$_{16-18}$alkyleneglycol 272 g were heated and stirred at 60° C. for one hour. Isostearic acid 284 g was added, and the reaction mixture stirred an additional two hours. Then, toluene and isopropanol were distilled off at 100° C. under 8 mm Hg for one hour.

The product was a brown viscous liquid, and its structure was confirmed by I.R. analysis:

$\beta$C═O 1530 cm$^{-1}$, 1460 cm$^{-1}$

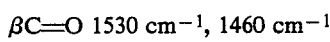

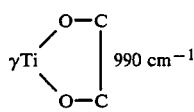

EXAMPLE B

Preparation of methoxy octyl tin C$_{12-14}$alkylene glycolate

Monooctyl tin trichloride 338 g and 500 g of xylene were stirred at 20°–40° C. and 580 g of 28% sodium methoxide in methanol solution was added dropwise over one hour. After stirring for one hour, 215 g of C$_{12-14}$alkylene glycol 500 g of xylene solution was added dropwise over one hour. After stirring an additional one hour, the precipitated sodium chloride was filtered off. The filtrate was then heated up to 100° C., and methanol and xylene were distilled off under 8 mm Hg.

The product was a yellow viscous liquid, whose structure was confirmed by I.R. analysis:

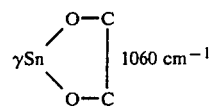

EXAMPLE C

Preparation of methoxy zirconium isooctoate C$_{10}$alkylene glycolate

Zirconium tetrachloride 233 g and 500 g of xylene were stirred at 20°–40° C. and 772 g of 28% sodium methoxide methanol solution was added over one hour. After stirring for an additional one hour, 202 g of C$_{10}$alkylene glycol 500 g of xylene solution was added dropwise over one hour. After stirring for one hour, 144 g of isooctanoic acid was added, and the mixture then stirred an additional two hours. The precipitated sodium chloride was filtered off, and the filtrate was heated up to 100° C. and methanol and xylene were distilled off under 8 mm Hg over one hour.

The product was a pale brown viscous liquid, whose structure was confirmed by I.R. analysis:

$\gamma$C═O 1550 cm$^{-1}$, 1460 cm$^{-1}$

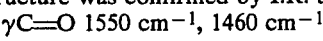

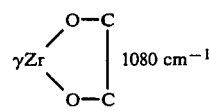

EXAMPLE D

Preparation of isopropoxy aluminum C$_{20-24}$alkylene glycolate

C$_{20-24}$Alkylene glycol 342 g xylene 600 g solution was added dropwise into a solution of 204 g of triisopropoxy aluminum and 500 g of xylene over 30 minutes. After stirring for one hour, xylene and isopropanol were distilled off at 100° C. under 8 mm Hg.

The product was a pale yellow semi-solid, whose structure was confirmed by I.R. analysis:

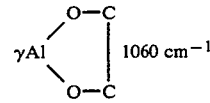

The amount of inorganic material used with the polymer forms no part of the instant invention, but in any case depends on the particular polymeric material, the inorganic material, and the property requirements of the finished products. From 10 to 3000 parts of inorganic material may be used, based on 100 parts of polymer, preferably from 20 to 2000, and most preferably from 20 to 250 parts per 100 parts of polymer.

When the inorganic material is pretreated with the metal glycolate, they can be dry blended or blended in an inert organic liquid or solvent. Examples include hydrocarbons such as hexane, heptane, octane, octene, benzene, toluene and xylene and chlorinated hydrocarbons such as trichloroethylene. The inorganic material and the metal glycolate may be admixed in any conventional type of intensive mixer, such as a Henschel or Hobart mixer or a Waring blender. Even hand mixing may be employed. The reaction proceeds rapidly at ambient temperature, but higher temperatures can be used for enhanced reaction and shorter reaction times, especially if reaction is slow at ambient temperature.

The treated inorganic material can be marketed as such, or combined or blended with an inert carrier. The carrier can improve handling properties of the metal glycolate. The carrier can be a solid, such as natural or synthetic hydrocarbon and fatty ester waxes, or liquid, which can be an inert organic liquid or solvent, as set forth above.

The amount of carrier is not critical. An amount within the range from 1 part up to about 10,000 parts per 100 parts of treated inorganic material, preferably, from about 100 parts to about 1000 parts per 100 parts inorganic material, can be used.

Synthetic resins that can be filled and/or pigmented with hydrophilic fillers and/or pigments whose surface is made hydrophobic by a metal glycolate according to this invention include α-olefin polymers such as polyethylene, polypropylene, polybutene, poly-3-methylbutene, or mixtures thereof and with copolymers other monomers such as ethylene-vinyl acetate copolymer; ethylene-propylene copolymer; polystyrene; polyvinyl acetate; polyacrylic esters; copolymers from styrene and another monomer (for example, maleic anhydride, butadiene, and acrylonitrile); acrylonitrile-butadiene-styrene copolymer, acrylic acid ester-butadiene-styrene copolymer, methacrylic acid ester-butadiene-styrene copolymer, polymethacrylate esters such as polymethacrylate; polyvinyl alcohol; polyvinyl formal; polyvinyl butyral; linear polyesters, polyamides; polycarbonates; polyacetals; polyurethanes; cellulosic resins; phenol-formaldehyde resins; urea-formaldehyde resins; melamine-formaldehyde resins; epoxy resins; unsaturated polyester resins; silicone resins; halogen-containing resins such as polyvinyl chloride, polyvinylidene chloride, polyvinylidene fluoride, and copolymers thereof, and rubbers such as isoprene rubber, butadiene rubber, epichlorohydrin rubber, chloroprene rubber, and blends of any of the above.

The polymers can also be combined with 2,2,6,6-tetraalkyl piperidyl stabilizers, and with conventional heat stabilizers, such as phenolic antioxidants, polyvalent metal salts of organic acids, organic phosphites, thioethers, and other known heat stabilizers.

Thus, for example, in the case of polyvinyl chloride resins, other polyvinyl chloride resin heat stabilizers can be included, including polyvalent metal fatty acid salts such as barium and cadmium salts of the higher fatty acids; organotin compounds; and epoxy compounds.

With polyolefin resins there can be employed fatty acid salts of polyvalent metals, and the higher fatty acid esters of thiodipropionic acids, such as, for example, dilauryl thiodipropionate.

With polyamide resin compositions, polyamide stabilizers such as copper salts in combination with iodides and/or other phosphorus compounds and salts of divalent manganese can be used.

With synthetic rubbers and acrylonitrile-butadiene-styrene terpolymers, other antioxidants and polyvalent metal salts of the higher fatty acids can be used.

In addition, other conventional additives for synthetic polymers, such as plasticizers, lubricants, emulsifiers, antistatic agents, flame-proofing agents, and pigments can be employed.

The following Examples illustrate the surface treatment of the invention applied to fillers for polymers, and the results of the treatment when the treated filler is incorporated in a polymer.

EXAMPLES 1 TO 5

One hundred grams of calcium carbonate having a nominal particle size of 1.8 microns was surface-treated with 1 g isopropyl tri(isostearoyl)titanate or 0.5 g, 1 g or 2 g of isopropoxy isostearoyloxy titanium $C_{16-18}$ alkylene glycolate, as shown in Table I. 100 grams of calcium carbonate was dispersed in 500 grams of n-hexane and the metal glycolate then added. The mixture was stirred for two hours at room temperature and then filtered. The treated calcium carbonate was washed with 200 grams of n-hexane and then dried.

Low density polyethylene 100 parts by weight and the treated calcium carbonate were then blended in a Henschel mixer and kneaded with a two-roll mill at 170° C. for ten minutes. The composition was compression-molded to prepare test specimens at 170° C. The tensile strength, elongation and melt flow index (MFI) were measured, and the results are shown in Table I:

TABLE I

| | Calcium carbonate | Amount (parts by weight) | Tensile strength (kg/cm$^2$) | Elongation (%) | MFI (g/10 min.) |
|---|---|---|---|---|---|
| Control | | | | | |
| 1 | Untreated | 50 | 107 | 50 | 0.87 |
| 2 | Untreated | 100 | 98 | 35 | 0.56 |
| 3 | Untreated | 150 | 90 | 5 | 0.12 |
| 4 | Treated with 1 g of isopropyl tri(isostearoyl)titanate | 50 | 105 | 60 | 1.56 |
| 5 | Treated with 1 g of isopropyl tri(isostearoyl)titanate | 100 | 95 | 43 | 0.94 |
| 6 | Treated with 1 g of isopropyl tri(isostearoyl)titanate | 150 | 87 | 15 | 0.48 |
| Example | | | | | |
| 1 | Treated with 0.5 g of titanium glycolate | 100 | 100 | 55 | 1.31 |
| 2 | Treated with 1 g of titanium glycolate | 50 | 105 | 75 | 2.45 |
| 3 | Treated with 1 g of titanium glycolate | 100 | 97 | 60 | 1.64 |
| 4 | Treated with 1 g of titanium glycolate | 150 | 92 | 32 | 0.93 |
| 5 | Treated with 2 g of titanium glycolate | 100 | 95 | 66 | 1.70 |

The titanium glycolate of the invention clearly is superior to the titanate of the prior art in preserving polymer strength and processability characteristics.

EXAMPLES 6 TO 21

One hundred grams of talc having a nominal particle size of 1.7 microns was surface treated with the titanate or the metal glycolate shown in Table II. 100 grams of talc was dispersed in 500 grams of n-hexane and the metal glycolate added. The mixture was stirred for two hours at room temperature and then filtered. The treated talc was washed with 200 grams of n-hexane and then dried.

Polypropylene 100 parts by weight and the treated talc were blended in a Henschel mixer and then kneaded in a two-roll mill for ten minutes. The composition was then injection-molded at 200° C., 5.1 kg/cm$^2$ to prepare test specimens. The tensile strength, elongation and MFI were measured, and the results are shown in Table II:

The metal glycolates of the invention are clearly superior to the titanate of the prior art in retaining polymer strength and processability.

EXAMPLES 22 TO 39

One hundred grams of aluminum hydrate having a nominal particle size of 1 micron was surface-treated with 1 g of the titanate or metal glycolate shown in Table III. 100 grams of aluminum hydrate was dispersed in 500 grams of n-hexane and the metal glycolate added. The mixture was stirred for two hours at room temperature and then filtered. The treated aluminum hydrate was washed with 200 grams of n-hexane and then dried.

High density polyethylene 100 parts by weight and the treated aluminum hydrate were then blended in a Henschel mixer followed by mixing in a Banbury mixer. The resulting composition was injection-molded at 200° C. and 300 kg/cm$^2$ to prepare test specimens. The Charpy impact strength and MFI were measured, and the results are shown in Table III:

TABLE II

|  | Surface treatment | Amount of treated talc | Tensile strength | Elongation | MFI |
|---|---|---|---|---|---|
| Control | | | | | |
| 1 | None | 50 | 486 | 9.4 | 2.54 |
| 2 | None | 70 | 423 | 2.3 | 0.91 |
| 3 | Isopropyl tri(isostearoyloxy) titanate | 50 | 386 | 9.5 | 2.61 |
| Example | | | | | |
| 6 | Isopropoxy isostearoyloxy titanium C$_{16-18}$ alkylene glycolate | 50 | 380 | 20.2 | 6.02 |
| 7 | | 70 | 385 | 6.3 | 2.17 |
| 8 | Isopropoxy isostearoyloxy titanium C$_{12-14}$ alkylene glycolate | 50 | 370 | 18.6 | 5.78 |
| 9 | | 70 | 390 | 5.3 | 1.98 |
| 10 | Ethoxytitanium dioctyl pyrophosphate C$_{12-14}$ alkylene glycolate | 50 | 380 | 18.2 | 5.42 |
| 11 | | 70 | 405 | 5.8 | 2.30 |
| 12 | Isopropoxy titanium dodecyl mercaptide C$_{16-18}$ alkylene glycolate | 50 | 378 | 15.6 | 4.85 |
| 13 | | 70 | 391 | 5.6 | 2.30 |
| 14 | Methoxy octyltin C$_{16-18}$ alkylene glycolate | 50 | 365 | 15.9 | 4.69 |
| 15 | | 70 | 376 | 5.2 | 2.85 |
| 16 | Methoxy octyl tin C$_{12-14}$ alkylene glycolate | 50 | 382 | 16.7 | 5.28 |
| 17 | Isopropoxy tin dodecylbenzenesulfonate C$_{16-18}$ alkylene glycolate | 50 | 395 | 18.1 | 6.43 |
| 18 | Isopropoxy zirconium isostearate C$_{16-18}$ alkylene glycolate | 50 | 392 | 20.1 | 6.18 |
| 19 | Methoxy zirconium dioctyl pyrophosphate C$_{16-18}$ alkylene glycolate | 50 | 388 | 20.6 | 6.16 |
| 20 | Diisopropoxy zirconium C$_{18}$ alkylene glycolate | 50 | 378 | 19.6 | 4.78 |
| 21 | Isopropoxy aluminum C$_{20-24}$ alkylene glycolate | 50 | 382 | 17.5 | 5.12 |

TABLE III

|  | Surface treatment | Amount of treated aluminum hydrate (parts by weight) | Impact strength (kg/cm/cm$^2$) | MFI (g/10 min.) |
|---|---|---|---|---|
| Control | | | | |
| 1 | None | 100 | 1.4 | 1.1 |
| 2 | None | 200 | — | — |
| 3 | Isopropyl tri(isostearoyl) titanate | 100 | 4.6 | 3.1 |
| 4 | | 200 | 1.4 | 0.3 |
| Example | | | | |
| 22 | Methoxy titanium isostearate C$_{10}$ alkylene glycolate | 100 | 5.2 | 5.9 |
| 23 | | 200 | 1.9 | 2.5 |
| 24 | Ethoxy titanium dioctyl phosphate C$_{16-18}$ alkylene glycolate | 100 | 4.9 | 5.2 |
| 25 | Ethoxy titanium 2-ethylhexyl-thioglycolate C$_{16-18}$ alkylene glycolate | 100 | 5.3 | 7.2 |
| 26 | Titanium glycolate C$_{16-18}$ alkylene glycolate | 100 | 6.7 | 5.2 |
| 27 | | 200 | 2.2 | 3.1 |
| 28 | Isopropoxy titanium β-oxypropionate C$_{16-18}$ alkylene glycolate | 100 | 5.6 | 7.1 |
| 29 | Methoxy octyl tin C$_{16-18}$ alkylene | 100 | 6.0 | 7.2 |

TABLE III-continued

| | Surface treatment | Amount of treated aluminum hydrate (parts by weight) | Impact strength (kg/cm/cm$^2$) | MFI (g/10 min.) |
|---|---|---|---|---|
| 30 | glycolate | 200 | 2.0 | 3.2 |
| 31 | Butoxy (butoxycarbonylethyl)tin C$_{16-18}$ alkylene glycolate | 100 | 5.8 | 6.8 |
| 32 | Tin β-mercaptopropionate C$_{16-18}$ alkylene glycolate | 100 | 5.6 | 6.5 |
| 33 | Dibutoxy zirconium C$_{16-18}$ alkylene | 100 | 5.7 | 5.9 |
| 34 | glycolate | 200 | 2.4 | 4.0 |
| 35 | Ethoxy zirconium dioctyl pyrophosphate C$_{10}$ alkylene glycolate | 100 | 5.4 | 7.1 |
| 36 | Ethoxy zirconium dodecylbenzene-sulfonate C$_{12-14}$ alkylene glycolate | 100 | 5.2 | 7.6 |
| 37 | Ethoxy zirconium oleate C$_{16-18}$ alkylene glycolate | 100 | 5.4 | 5.8 |
| 38 | Isopropoxy aluminum C$_{16-18}$ alkylene glycolate | 100 | 5.3 | 6.2 |
| 39 | Aluminum isostearate C$_{16-18}$ alkylene glycolate | 100 | 5.2 | 5.8 |

The metal glycolates of the invention are clearly superior to the titanate of the prior art in retaining polymer strength and processability.

EXAMPLES 40 TO 66

Calcium carbonate 100 parts by weight was treated with 0.7 or 1.4 parts by weight of the prior art surface-treatment agent or metal glycolate shown in Table IV. 100 grams of calcium carbonate was dispered in 500 grams of n-hexane and the metal glycolate then added. The mixture was stirred for two hours at room temperature and then filtered. The treated calcium carbonate was washed with 200 grams of n-hexane and then dried. The treated calcium carbonate 70 parts by weight was dispersed in 30 parts by weight of liquid paraffin, and the viscosity was measured. The results are shown in Table IV:

TABLE IV

| | Surface treatment | Amount of surface treatment agent (parts by weight) | Viscosity |
|---|---|---|---|
| Control | | | |
| 1 | Isopropyl tri(isostearoyl) | 0.7 | >5000 |
| 2 | titanate | 1.4 | 4500 |
| 3 | Isopropoxy titanium isostearate ethylene glycolate | 0.7 | 3600 |
| Example | | | |
| 40 | Isopropoxy titanium iso- | 0.7 | 540 |
| 41 | stearate C$_{16-18}$ alkylene glycolate | 1.4 | 380 |
| 42 | Isopropoxy titanium iso- | 0.7 | 710 |
| 43 | stearate C$_{10}$ alkylene glycolate | 1.4 | 420 |
| 44 | Diisopropoxy titanium C$_{16-18}$ alkylene glycolate | 0.7 | 820 |
| 45 | Methoxy titanium isostearate C$_{16-18}$ alkylene glycolate | 0.7 | 480 |
| 46 | Isopropoxy titanium dodecylbenzene-sulfonate C$_{18}$ alkylene glycolate | 0.7 | 520 |
| 47 | Isopropoxy titanium dioctyl phosphate C$_{16-18}$ alkylene glycolate | 0.7 | 780 |
| 48 | Ethoxy titanium oleoyloxy-ethylmercaptide C$_{10}$ alkylene glycolate | 0.7 | 880 |
| 49 | Isopropoxy titanium dodecyl-mercaptide C$_{16-18}$ alkylene glycolate | 0.7 | 910 |
| 50 | Titanium β-oxypropionate | 0.7 | 580 |
| 51 | C$_{16-18}$ alkylene glycolate | 1.4 | 420 |
| 52 | Isopropoxy tin dodecylbenzene | 0.7 | 850 |
| 53 | sulfonate C$_{16-18}$ alkylene glycolate | 1.4 | 590 |
| 54 | Butoxy tin isostearate C$_{16-18}$ alkylene glycolate | 0.7 | 820 |
| 55 | Butoxy tin dioctyl pyrophosphate C$_{16-18}$ alkylene glycolate | 1.4 | 600 |
| 56 | Methoxy octyl tin C$_{16-18}$ alkylene glycolate | 0.7 | 790 |
| 57 | Methoxy tin β-oxypropionate C$_{16-18}$ alkylene glycolate | 0.7 | 810 |
| 58 | Dioctyl tin C$_{20}$ alkylene glycolate | 0.7 | 950 |
| 59 | Stearyloxy zirconium isostearate C$_{12-14}$ alkylene glycolate | 1.4 | 580 |
| 60 | Isopropoxy zirconium isostearate C$_{12-14}$ alkylene glycolate | 1.4 | 540 |
| 61 | Methoxy zirconium dioctylpyrophosphate C$_{16-18}$ alkylene glycolate | 0.7 | 630 |

TABLE IV-continued

| | Surface treatment | Amount of surface treatment agent (parts by weight) | Viscosity |
|---|---|---|---|
| 62 | Isopropoxy zirconium dodecyl-mercaptide C$_{12-14}$ alkylene glycolate | 0.7 | 810 |
| 63 | Ethoxy zirconium acrylate C$_{16-18}$ alkylene glycolate | 0.7 | 780 |
| 64 | Zirconium glycolate C$_{16-18}$ alkylene glycolate | 0.7 | 820 |
| 65 | Aluminum isostearate C$_{16-18}$ alkylene glycolate | 0.7 | 950 |
| 66 | Butoxy aluminum C$_{12-14}$ alkylene glycolate | 0.7 | 820 |

The metal glycolates of the invention are clearly superior to the titanate of the prior art in retaining polymer strength and processability.

EXAMPLES 67 TO 71

These Examples show the effect of the length of alkyl chain in the alkylene glycol on the metal glycolate, in the metal glycolate of the formula:

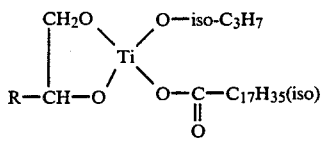

One hundred grams of talc having a nominal particle size of 1.7 microns was surface treated with the titanate or the metal glycolate shown in Table V. 100 grams of talc was dispersed in 500 grams of n-hexane and the metal glycolate added. The mixture was stirred for two hours at room temperature and then filtered. The treated talc was washed with 200 grams of n-hexane and then dried.

Polypropylene 100 parts by weight and the treated talc were blended in a Henschel mixer and then kneaded in a two-roll mill for ten minutes. The composition was then injection-molded at 200° C., 5.1 kg/cm$^2$ to prepare test specimens. The tensile strength, elongation and MFI were measured, and the results are shown in Table V:

TABLE V

| | R | Amount of treated talc (parts by weight) | Tensile strength (kg/cm$^2$) | Elongation (%) | MFI (g/10 min.) |
|---|---|---|---|---|---|
| Control | | | | | |
| 1 | H | 50 | 388 | 9.4 | 2.54 |
| 2 | CH$_3$ | 50 | 385 | 9.7 | 2.77 |
| 3 | C$_4$H$_9$ | 50 | 386 | 10.6 | 3.05 |
| 4 | C$_6$H$_{13}$ | 50 | 380 | 11.4 | 3.52 |
| Example | | | | | |
| 67 | C$_{10}$H$_{21}$ | 50 | 382 | 16.5 | 5.34 |
| 68 | C$_{10-12}$H$_{21-25}$ | 50 | 370 | 18.6 | 5.78 |
| 69 | C$_{14-16}$H$_{29-33}$ | 50 | 380 | 20.2 | 6.02 |
| 70 | C$_{16}$H$_{33}$ | 50 | 378 | 21.0 | 6.11 |
| 71 | C$_{18-20}$H$_{37-41}$ | 50 | 375 | 20.3 | 5.95 |

The above results clearly show that the R alkyl should have at least eight carbon atoms.

Having regard to the foregoing disclosure the following is claimed as the inventive and patentable embodiments thereof:

1. A process for providing a hydrophobic surface on hydrophilic inorganic material which comprises applying to the surface of the hydrophilic inorganic material in particulate form an amount of at least 0.01 part per 100 parts of hydrophilic inorganic material, sufficient to provide a hydrophobic surface thereon, of a metal glycolate compound having the formula:

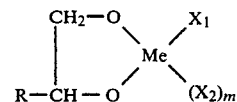

wherein:
Me is Sn, Ti, Zr or Al;
when Me is Sn, Ti or Zr, m is 1, and when Me is Al, m is 0;
R is alkyl having from about eight to about fifty carbon atoms;
X$_1$ and X$_2$ are independently selected from the group consisting of —R$_1$, —OR$_1$, —OCOR$_1$, —SR$_1$, —S(CH$_2$)$_n$COOR$_1$, —OSO$_2$—R$_1$, —SR$_2$OCOR$_1$,

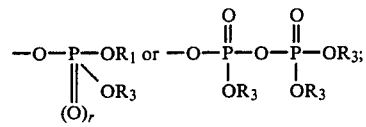

X$_1$ and X$_2$ can be combined to form

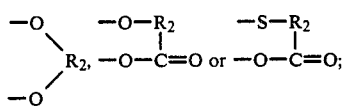

R$_1$ is selected from the group consisting of alkyl having from one to about eighteen carbon atoms; alkenyl having from three to about eighteen carbon atoms; cycloalkyl having from five to about eight carbon atoms; and aryl and alkaryl having from six to about eighteen carbon atoms;

$R_2$ is alkylene having from one to about fifty carbon atoms;

$R_3$ is selected from the group consisting of hydrogen, alkyl having from one to about eighteen carbon atoms; alkenyl having from three to about eighteen carbon atoms; cycloalkyl having from five to about eight carbon atoms; and aryl and alkaryl having from six to about eighteen carbon atoms;

r is 0 or 1.

2. A process according to claim 1 in which the metal glycolate compound is applied as a solution thereof in an inert solvent.

3. A process according to claim 1 in which the metal glycolate compound is applied by dry blending with the hydrophilic inorganic material.

4. A process according to claim 1, carried out at ambient temperature.

5. A process according to claim 1, carried out with heating above ambient temperature.

6. A composition for providing a hydrophobic surface on hydrophilic inorganic material in particulate comprising a metal glycolate compound having the formula:

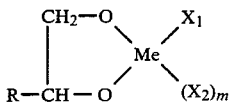

wherein:

Me is Sn, Ti, Zr or Al;

when Me is Sn, Ti or Zr, m is 1, and when Me is Al, m is 0;

R is alkyl having from about eight to about fifty carbon atoms;

$X_1$ and $X_2$ are independently selected from the group consisting of $-R_1$, $-OR_1$, $-OCOR_1$, $-SR_1$, $-S(CH_2)_nCOOR_1$, $-OSO_2-R_1$, $-SR_2OCOR_1$,

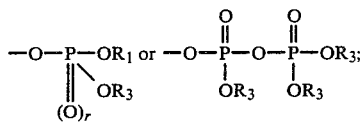

$X_1$ and $X_2$ can be combined to form

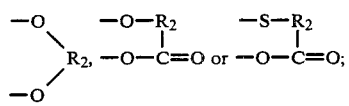

$R_1$ is selected from the group consisting of alkyl having from one to about eighteen carbon atoms; alkenyl having from three to about eighteen carbon atoms; cycloalkyl having from five to about eight carbon atoms; and aryl and alkaryl having from six to about eighteen carbon atoms;

$R_2$ is alkylene having from one to about fifty carbon atoms;

$R_3$ is selected from the group consisting of hydrogen, alkyl having from one to about eighteen carbon atoms; alkenyl having from three to about eighteen carbon atoms; cycloalkyl having from five to about eight carbon atoms; and aryl and alkaryl having from six to about eighteen carbon atoms;

r is 0 or 1; and an inert liquid carrier for the metal glycolate compound.

7. A metal glycolate compound having the formula:

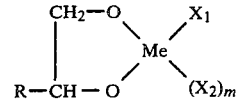

wherein:

Me is Sn, Ti, Zr or Al;

when Me is Sn, Ti or Zr, m is 1, and when Me is Al, m is 0;

R is alkyl having from about eight to about fifty carbon atoms;

$X_1$ and $X_2$ are independently selected from the group consisting of $-R_1$, $-OR_1$, $-OCOR_1$, $-SR_1$, $-S(CH_2)_nCOOR_1$, $-OSO_2-R_1$, $-SR_2OCOR_1$,

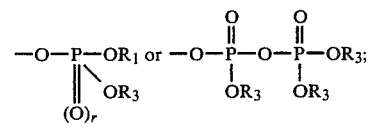

$X_1$ and $X_2$ can be combined to form

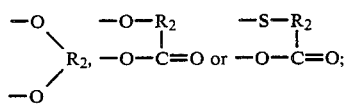

$R_1$ is selected from the group consisting of alkyl having from one to about eighteen carbon atoms; alkenyl having from three to about eighteen carbon atoms; cycloalkyl having from five to about eight carbon atoms; and aryl and alkaryl having from six to about eighteen carbon atoms;

$R_2$ is alkylene having from one to about fifty carbon atoms;

$R_3$ is selected from the group consisting of hydrogen, alkyl having from one to about eighteen carbon atoms; alkenyl having from three to about eighteen carbon atoms; cycloalkyl having from five to about eight carbon atoms; and aryl and alkaryl having from six to about eighteen carbon atoms;

r is 0 or 1.

8. A metal glycolate compound according to claim 7, in which Me is Sn, Ti or Zr and m is 1.

9. A metal glycolate compound according to claim 7, in which Me is Al and m is 0.

10. A metal glycolate compound according to claim 7, in which at least one of $X_1$ and $X_2$ is $R_1$.

11. A metal glycolate compound according to claim 7, in which at least one of $X_1$ and $X_2$ is $OR_1$.

12. A metal glycolate compound according to claim 7, in which at least one $X_1$ and $X_2$ is $OCOR_1$.

13. A metal glycolate compound according to claim 7, in which at least one of $X_1$ and $X_2$ is $SR_1$.

14. A metal glycolate compound according to claim 7, in which at least one of $X_1$ and $X_2$ is $S(CH_2)_nCOOR_1$.

15. A metal glycolate compound according to claim 7, in which at least one of $X_1$ and $X_2$ is $OSO_2R_1$.

16. A metal glycolate compound according to claim 7, in which at least one of $X_1$ and $X_2$ is $SR_2OCOR_1$.

17. A metal glycolate compound according to claim 7, in which at least one of $X_1$ and $X_2$ is

18. A metal glycolate compound according to claim 7, in which at least one of $X_1$ and $X_2$ is

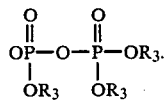

19. A metal glycolate compound according to claim 7, in which $X_1$ and $X_2$ form

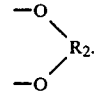

20. A metal glycolate compound according to claim 7, in which $X_1$ and $X_2$ form

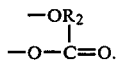

21. A metal glycolate compound according to claim 7, in which $X_1$ and $X_2$ form

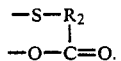

* * * * *